(12) United States Patent
Anderson

(10) Patent No.: US 7,270,971 B2
(45) Date of Patent: Sep. 18, 2007

(54) FLUORESCENCE ASSAY FOR MEASURING THE RATE OF CHOLESTEROL ESTER TRANSFER

(75) Inventor: Matt S. Anderson, Berkeley Heights, NJ (US)

(73) Assignee: Merck & Co., Inc., Rahway, NJ (US)

( * ) Notice: Subject to any disclaimer, the term of this patent is extended or adjusted under 35 U.S.C. 154(b) by 333 days.

(21) Appl. No.: 10/966,628

(22) Filed: Oct. 15, 2004

(65) Prior Publication Data

US 2005/0084920 A1    Apr. 21, 2005

Related U.S. Application Data

(60) Provisional application No. 60/511,983, filed on Oct. 16, 2003.

(51) Int. Cl.
*C12Q 1/60*    (2006.01)

(52) U.S. Cl. ...................................................... 435/11

(58) Field of Classification Search ................... 435/11
See application file for complete search history.

(56) References Cited

U.S. PATENT DOCUMENTS

| | | | |
|---|---|---|---|
| 5,585,235 A | 12/1996 | Brocia | |
| 5,618,683 A | 4/1997 | Brocia et al. | |
| 5,770,355 A | 6/1998 | Brocia | |
| 2006/0040999 A1* | 2/2006 | Ali et al. | ..................... 514/376 |

OTHER PUBLICATIONS

Epps, D. et al. Method for Measuring the Activities of Cholesteryl Ester Transfer Protein. Chemistry and Physics of Lipids vol. 77, 51-63, 1995.*
Bisgaier C. et al. Use of Fluorescent Cholesteryl Ester Microemulsions in Cholesteryl Ester Transfer Protein Assays. J of Lipid Research. vol. 34 1625-1634, 1993.*
D.E. Epps et al., "Method for Measuring the Activities of Cholesteryl Ester Transfer Protein (Lipid Transfer Protein)", Chemistry and Physics of Lipids, 77(1995), pp. 51-63.

* cited by examiner

*Primary Examiner*—Ralph Gitomer
(74) *Attorney, Agent, or Firm*—James L. McGinnis; Mark Daniel

(57) ABSTRACT

An improved method of obtaining fluorescence measurements which may be used as a measure of the CETP-catalyzed rate of transfer of a lipophilic non-polar fluorescent cholesteryl ester between lipoprotein particles is disclosed. The method may be used in assays for screening CETP inhibitors.

13 Claims, 1 Drawing Sheet

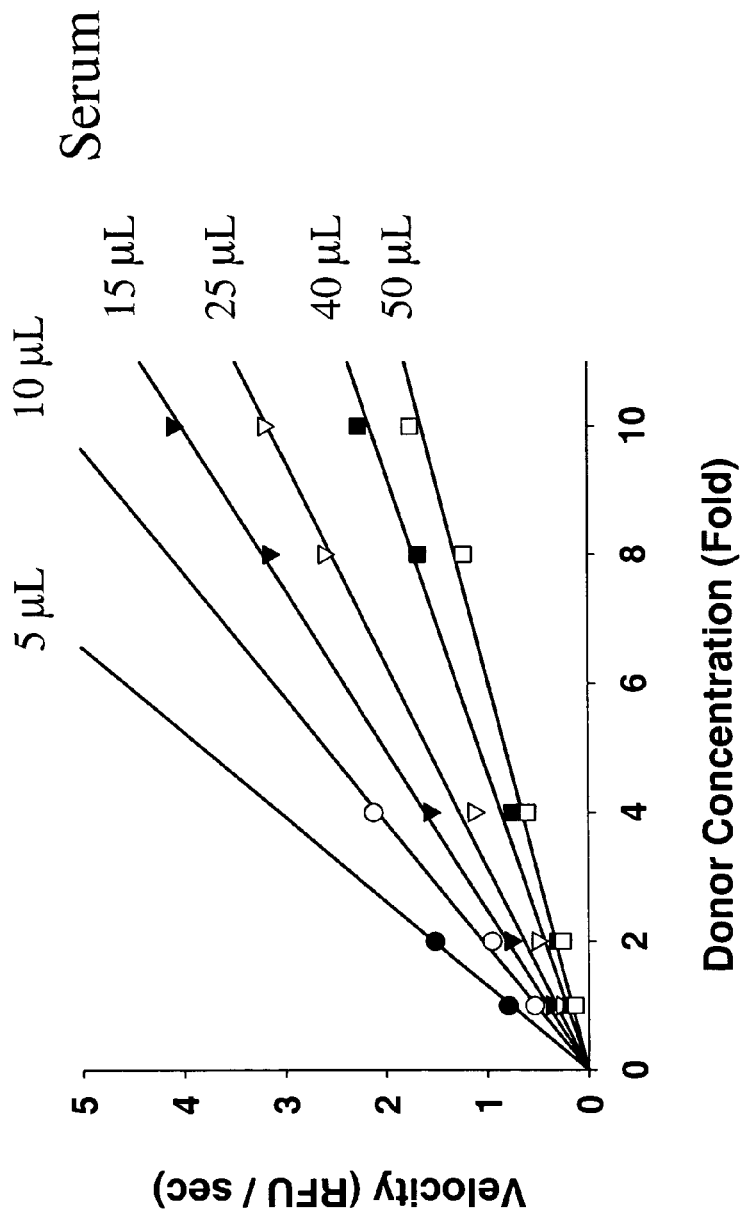

FLUORESCENCE ASSAY FOR MEASURING THE RATE OF CHOLESTEROL ESTER TRANSFER

CROSS REFERENCE TO RELATED APPLICATIONS

This application claims priority under 35 U.S.C. §119(e) from U.S. application Ser. No. 60/511,983, filed Oct. 16, 2003.

FIELD OF THE INVENTION

The instant invention relates to a fluorescence assay that can be used to measure the rate of transfer of a cholesterol ester between lipoprotein particles.

BACKGROUND OF THE INVENTION

Cholesteryl ester transfer protein (CETP) is a plasma glycoprotein that catalyzes the transfer of triglycerides (TG) and cholesteryl esters (CE) between circulating lipoproteins (see Hesler, C. B., et. al. (1987) *Purification and characterization of human plasma cholesteryl ester transfer protein. J. Biol. Chem.* 262(5), 2275-2282), particularly between high density lipoproteins (HDL) and low density lipoproteins (LDL). The transfer of these neutral lipids is driven by their concentration gradients, hence net cholesteryl ester transfer occurs from HDL to very low density lipoproteins (VLDL), intermediate density lipoproteins (IDL) and LDL with an obligate transfer of triglyceride in return. The mechanism by which these movements are facilitated is a matter of ongoing debate. The catalytic activities performed by CETP were identified as distinct from those performed by a related plasma protein, phospholipid transfer protein (PLTP), and subsequent research has demonstrated the independence of these two activities in vivo.

In humans, CETP plays a role in reverse cholesterol transport, the process whereby cholesterol is returned to the liver from peripheral tissues. Intriguingly, many animals do not possess CETP including animals with high HDL levels known to be resistant to coronary heart disease such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120(3), 517-525). Numerous epidemiologic studies correlating the effects of natural variation in CETP activity with respect to coronary heart disease risk have been performed including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL concentration and CETP activity (see Inazu, A., et. al. (2000) *Cholesteryl ester transfer protein and atherosclerosis, Curr. Opin. Lipidol.* 11(4), 389-396), leading to speculation that pharmacologic inhibition of CETP activity could be beneficial to humans by driving an improved circulating lipid profile.

However, epidemiologic studies have yet to provide an unequivocal validation of this concept. Importantly, the case of human CETP null mutants has provided evidence that the HDL formed in such humans is deficient in its interactions with the HDL receptor SR-B1 (see Ishigami, M., et al. (1994) *Large and cholesteryl ester rich high density lipoproteins in cholesterol ester transfer protein deficiency can not prevent macrophages from cholesterol accumulation induced by acetylated low density lipoproteins, J. Biochem.* (Tokyo) 116, 257-262), an effect that could undermine the benefit of associated HDL raising.

New classes of CETP inhibitors are being searched for using high throughput screening methods and are then being investigated with the goals of finding active inhibitors that may be useful as medications and that may validate inhibition of CETP as a method of reducing the risk of atherosclerosis by improving the HDL/LDL cholesterol ratio.

Assays that are currently in use for measuring the activity of CETP are not readily adapted to high throughput screening. The current invention provides a fluorescence assay that is sensitive enough to measure changes in the activity of CETP in the presence of compounds that are being screened as inhibitors. A fluorescence assay that was published by D. E. Epps et al. may be used, but the amount of "noise" in the measurements makes it very difficult to measure small changes in the transfer rate. See Epps, et al. (1995) *Method for measuring the activities of cholesteryl ester transfer protein (lipid transfer protein), Chem. Phys. Lipids,* 77, 51-63. The current invention significantly improves the assay that was originally published by Epps, et al. The publication by Epps, et al. is incorporated by reference into this application.

In the method of Epps, a donor particle was made by incorporating a cholesteryl ester of a fluorescent BODIPY® dye (BODIPY-CE) into a synthetic HDL particle, along with human apoHDL, hen egg L-α-phosphatidylcholine, and hexabromotriolein (HBT). Acceptor particles were similar, except that they did not include BODIPY-CE, and they contained triolein rather than HBT. BODIPY is a fluorescent molecule which self-quenches in a concentration dependent manner. BODIPY-CE is a lipophilic non-polar cholesteryl ester which is similar enough to the cholesteryl esters in HDL and LDL to be transported by CETP. The rate of transfer of BODIPY-CE from donor particles to acceptor particles was determined by measuring changes in fluorescence as the BODIPY-CE migrated from the donor to the acceptor particle. BODIPY-CE fluoresces only minimally in the donor particle because of self-quenching. It becomes fluorescent as it migrates away from the donor particle to the LDL particle, where its concentration is low, so that it no longer self-quenches. However, there is typically enough background fluorescence from the BODIPY-CE in the donor particle that there is significant baseline noise, so that the measurements are very difficult to perform accurately.

SUMMARY OF THE INVENTION

A method of measuring fluorescence, where the fluorescence may be used to measure the CETP catalyzed transfer of a non-polar fluorescent ester between lipoprotein particles, is provided herein. The method comprises the steps of:

(A) Preparing a suspension containing:

(1) A synthetic donor lipoprotein particle which comprises (a) a lipophilic non-polar fluorescent ester, (b) an apolipoprotein, (c) a fluorescence quencher which is effective in quenching the fluorescence emitted by the lipophilic non-polar fluorescent ester and is stable to diffusion, (d) a triglyceride, and (e) a phospholipid;

(2) An acceptor lipoprotein particle which is selected from a native lipoprotein particle and a synthetic high density lipoprotein particle; and (3) A buffered solution which contains CETP;

(B) Irradiating the suspension with light which stimulates fluorescence from the fluorescent ester; and (C) Measuring the fluorescence from the suspension at one or more times after the suspension is prepared. These measurements are taken while the suspension is still under irradiation.

BRIEF DESCRIPTION OF THE DRAWINGS

FIG. 1 shows a plot of multiple assays using the protocol of Example 2.

DETAILED DESCRIPTION OF THE INVENTION

In the method of measuring fluorescence as described above, the lipophilic non-polar fluorescent ester is generally a cholesteryl ester (CE). The lipophilic non-polar fluorescent ester generally comprises the fluorescent heterocyclic BODIPY ring system. The preferred lipophilic non-polar fluorescent ester is BODIPY-CE®.

The synthetic donor particle is generally a synthetic HDL particle. The donor particle is referred to as a donor because it is the source of BODIPY-CE in the CE transfer reaction. Transfer of the fluorescent ester from the donor particles can be measured by changes in the fluorescence of the BODIPY groups. The acceptor particle receives the lipophilic non-polar fluorescent ester in the transfer reaction. The acceptor may be a native lipoprotein particle or a synthetic HDL particle. Native lipoproteins include native HDL particles, native LDL particles, native VLDL particles, and native IDL particles. Native LDL particles generally are isolated as lipoprotein particles having a density less than 1.063 g/ml. This fraction includes LDL, VLDL, and IDL, but VLDL and IDL can also be isolated as separate fractions. In most cases the synthetic donor particle is a synthetic HDL particle. In most cases the acceptor particle is a native LDL particle, which is more conveniently isolated than VLDL and IDL particles.

In this method of measuring fluorescence, the fluorescence quencher is effective in quenching >85% of the fluorescence emitted by the lipophilic non-polar fluorescent ester. The fluorescence quencher is stable to diffusion, so that >95% of the quencher remains (or would remain if stored) in the donor particle for time periods that allow storage, for example at least one week and preferably at least one month after the donor particle is prepared. Preferably, the fluorescence quencher is stable to diffusion, so that >98% of the quencher remains (or would remain if stored) in a donor particle for at least one week, and preferably at least one month after the donor particle is prepared. The fluorescence quencher is stable to both uncatalyzed diffusion and also diffusion that is facilitated by a catalyst, such as CETP.

The CETP that is used in this method can be obtained and used in a number of forms. Native human CETP can be used in human plasma or serum. Recombinant human CETP can also be obtained from recombinant CETP grown in other mammalian cells, such as CHO. The recombinant CETP can be used in this assay either in serum or plasma, or it can be obtained in buffered solutions that are essentially free of serum and plasma.

Most often in this method of measuring fluorescence, the donor particle is a synthetic HDL particle which comprises (a) BODIPY-CE, (b) apoHDL, (c) a fluorescence quencher which is effective in quenching >85% of the fluorescence emitted by the lipophilic non-polar fluorescent ester and is stable to diffusion so that >95% of said quencher remains in a donor particle for at least one month after the donor particle is synthesized, (d) a triglyceride, and (e) a phospholipid;

the acceptor particle is a native LDL particle; and the buffered solution comprises recombinant or native human CETP.

In all of the embodiments of this method, the preferred fluorescence quencher is 4-(4-(dimethylaminophenyl)azo) benzoic acid, dicetylamide.

The invention also is a method of measuring the rate of the CETP-catalyzed transfer of a lipophilic non-polar fluorescent cholesteryl ester between lipoprotein particles by the steps of:

(A) Preparing a suspension which contains:

(1) A synthetic donor lipoprotein particle which comprises (a) a lipophilic non-polar fluorescent cholesteryl ester containing a BODIPY group, (b) an apolipoprotein, (c) a fluorescence quencher, which is effective in quenching the fluorescence emitted by the lipophilic non-polar fluorescent ester and is stable to diffusion, (d) a triglyceride, and (e) a phospholipid;

(2) An acceptor lipoprotein particle selected from a native lipoprotein particle and a synthetic high density lipoprotein particle; and (3) A buffered solution which contains CETP;

(B) Irradiating the suspension with light at a wavelength which stimulates fluorescence from the fluorescent ester;

(C) Measuring the fluorescence from the fluorescent ester at one or more times after the suspension is prepared; and (D) Computing the rate of transfer of the cholesteryl ester containing a BODIPY group from the donor particle using the fluorescence measurements of step (C).

In preferred embodiments of this method, the synthetic donor lipoprotein particle is a synthetic HDL particle which comprises apoHDL as the apolipoprotein;

the lipophilic non-polar fluorescent cholesteryl ester is BODIPY-CE; and the acceptor lipoprotein particle is native LDL.

In preferred embodiments, the fluoresence quencher is 4-(4-(dimethylaminophenyl)azo)benzoic acid, dicetylamide.

Variations in the method of measuring fluorescence described previously can also be used in this method of measuring the rate of CETP-catalyzed transfer of a non-polar fluorescent ester.

This assay measures the cholesteryl ester (CE) transfer reaction using a synthetic donor particle similar in size and density to HDL. The core of the fluorescent donor particle is the fluorescent BODIPY moiety, which is 4,4-difluoro-4-bora-3a,4a-diaza-s-indacene. The preferred BODIPY fluorescent molecule is cholesteryl 4,4-difluoro-5,7-dimethyl-4-bora-3a,4a-diaza-s-indacene-3-dodeca (BODIPY®-CE). The assay is run in the presence of light having a wavelength of about 480-485 nm, which provides excitation of the fluorescent BODIPY-CE, which has a maximum absorption at 505 nm. The fluorescence is measured at about 511-512 nm. BODIPY-CE is a self-quenching fluorescent compound, so that a high concentration of BODIPY-CE in the donor particle quenches fluorescence from the donor particle. A second quencher in addition to BODIPY-CE is also included in the donor particle, such as for example, 4-(4-(dimethylaminophenyl)azo)benzoic acid, dicetyl amide, which is also referred to herein as dabcyl dicetylamide. Native lipoprotein particles (e.g. LDL) are used as acceptors of BODIPY-CE. Molecules of BODIPY-CE that are removed from the donor and then transferred to the acceptor particles are no longer quenched and become fully fluorescent at 512 nm. The increase in fluorescence signal as this occurs is monitored with time. Although BODIPY-CE is self-quenching, it still exhibits enough fluorescence that the background fluorescence from the donor particles is high without an added quencher. The baseline fluorescence in the donor particle is greatly reduced when a quencher in addition to BODIPY-CE quencher is included. Because of the reduced background fluorescence, the use of the assay reagents as described allows for the assay of the CE transfer half-reaction in the presence of serum or plasma (e.g. up to 33% serum or plasma may be present in the buffer).

It will be appreciated by one of skill in the art that the assay does not directly measure the rate of the CE transfer half-reaction, and that there is also a computation required to determine the rate of CE transfer. The fluorescence data that is obtained from the assay is approximately proportional to the amount (e.g. concentration) of the fluorescent probe which has diffused from the donor particle to the acceptor particle. The rate of transfer of the fluorescent probe can readily be computed based on the fluorescence data. The assay is particularly useful for measuring changes in CETP-catalyzed transfer of cholesteryl esters from HDL particles to acceptor particles, such as LDL particles, in the presence of substances that are being tested as inhibitors of the CETP-catalyzed transfer reaction. The changes in rates of transfer when test inhibitors of CETP-catalyzed transfer are present are readily measured as % inhibition of the transfer half-reaction by comparing the changes in fluorescence with and without the compound being tested as an inhibitor. This is explained in the Data Evaluation section of Example 1.

It will also be appreciated by one of skill in the art that this method is used to measure the CE transfer reaction. There is also a second corresponding transfer reaction in which triglycerides are transferred between particles. These two transfer reactions are often referred as "half-reactions."

The use of the fluorescence quencher greatly improves the assay. For example, in a typical control experiment without the added quencher, the background fluorescence is about 623 Relative Fluorescence Units (RFU), whereas the maximum fluorescence radiation, including background, is about 1500 RFU after the BODIPY-CE has diffused out of the donor particles. With an added quencher, greater than 75% of the residual background fluorescence that is still present after self-quenching is eliminated, and preferably greater than 85% of the background fluorescence is eliminated, so that there is little or no observable background fluorescence.

Other BODIPY cholesteryl esters may also be used for studies at different wavelengths. Various BODIPY compounds fluoresce in the range of about 485-570 nm. Fluorescent molecules that do not include the BODIPY group may be used, provided that a fluorescent molecule can be found that does not bleach or react under irradiation. Practically speaking, the BODIPY compounds are the best fluorescent molecules for this application. Other quenchers may also be used for studies using different fluorescent probes or at the wavelength characteristic of BODIPY-CE. Other quenchers would be selected with the criteria that they do not diffuse out of the donor particles, they are not transferred out of the donor particles by CETP, they can be incorporated into the synthetic HDL particles, they are effective in quenching the fluorescence without otherwise interfering with the assay, and they do not chemically react or bleach when they are exposed to the light that is used to excite them.

This assay is particularly useful for measuring the rate of CETP catalyzed transfer of cholesteryl esters and changes in the rate of transfer of cholesteryl esters in the presence of compounds that are being tested as potential inhibitors of CETP catalysis. BODIPY-CE is transferred by CETP, and it therefore can be used as a model of a cholesteryl ester that is being transferred.

Finally, it will be recognized by a practitioner in the field that the synthetic lipoprotein particles that are used in the above methods are also new. These particles include a lipophilic non-polar fluorescent cholesteryl ester (e.g. BODIPY-CE), an apolipoprotein (e.g. HDL), a fluorescence quencher, a triglyeride, and a phospholipid.

The suspensions containing the synethetic donor lipoproteins described immediately above in combination with acceptor lipoprotein particles and a buffered solution comprising CETP, are also new.

DEFINITIONS

BODIPY-CE, the fluorescent molecular probe used in these experiments, is cholesteryl 4,4-difluoro-5,7-dimethyl-4-bora-3a,4a-diaza-s-inddacene-3-dodecanoate.

BODIPY is the fluorescent heterocyclic ring system in the molecular probe.

DOPC is Dioleyl phosphatidyl choline.

Triolein is the trioleyl ester of glycerol.

Dabcyl dicetylamide is 4-(4-(dimethylaminophenyl)azo) benzoic acid, dicetylamide.

These and other terms that are used herein are well known to practitioners in the fields of biochemistry and medicinal chemistry.

EXAMPLES

Assay Components:

1) Donor Particles

Synthetic donor particles contain DOPC, BODIPY-CE (Molecular Probes, C-3927), triolein (a triglyceride), dabcyl dicetylamide, and apoHDL. DOPC and triolein were obtained from Sigma. Dabcyl dicetylamide was made by heating dabcyl N-succinimide with dicetylamine in DMF at 95° C. overnight in the presence of diisopropylamine catalyst. All lipids were made or obtained as stocks in ethanol. ApoHDL was obtained from native human HDL as described in Epps et al. (1995) *Method for measuring the activities of cholesteryl ester transfer protein (lipid transfer protein)*, Chem. Phys. Lipids, 77, 51-63, and was resuspended in 50 mM Tris hydrochloride, pH 8.6, containing 150 mM sodium chloride and 1 mM ethylenediaminetetraacetic acid (EDTA) by the method of A. Scanu (1966) *Forms of human serum high density lipoprotein protein*, J. Lipid Res, 7, 295-306; it was then sterile filtered and stored at 4° C. Appropriate amounts of solvent stocks of DOPC, BODIPY-CE, triolein, and dabcyl dicetylamide were dried down by evaporation of the solvent. The dried lipids were then resuspended in a buffered solution containing apoHDL and probe sonicated to form particles. Particles are fractionated by ultracentrifugation and those in the density range of 1.063-1.21 g/ml are collected, as described by Epps. Particle concentration is expressed in terms of protein concentration as determined by BCA protein assay. Particles are stored at 4° C. The particles are stable enough that they can be stored for an extended period of time (at least a month).

2) Acceptor Particles

Native lipoproteins from human blood are used as acceptor particles. Particles having a density less than 1.063 g/ml are collected by ultracentrifugation. These particles include VLDL, IDL, and LDL. Lipoprotein concentration is expressed in terms of protein concentration as determined by BCA protein assay (Pierce). Particles are stored at 4° C. These particles are stable enough that they can be stored for an extended period of time (at least a month).

3) Assay Buffer 1×

50 mM Tris pH 7.4

100 mM NaCl 1 mM EDTA

Example 1

Assay of CETP-catalyzed CE Transfer in Buffer

CETP Enzyme Source

Recombinant human CETP expressed in CHO cells was supplied by Cardiovascular Targets, Inc.

This CETP is substantially free of serum and plasma. Enzyme is stored frozen at −70° C.

Assay Conditions and Protocol

Assay Temperature: 25° C.

Final Concentrations in a 150 μL Volume:

5 ng/μl Donor Particles 17 ng/μl Acceptor Particles

1×assay buffer 0.8 nM CETP

2% DMSO or other solvent—if compounds are being tested

Protocol:

Dynex Microfluor 2 U-bottom black 96-well plates (Cat# 7205) are used.

An assay cocktail containing CETP and 1×buffer (100 μl) is transferred to a plate with a multichannel pipettor.

A compound being tested in solvent or a solvent control (3 μl volume) is added to the plate with a multichannel pipettor. Solvent for the test compound is generally DMSO. Test compounds may be preincubated in solvent (e.g. DMSO) for up to 15 minutes at 25° C.

The plate is mixed for 30 sec @ 850 rpm on Eppendorf Thermomixer R plate shaker.

A second assay cocktail containing donor, acceptor, and 1×buffer (47 μl) is transferred to the plate with a multichannel pipettor to start the assay. The plate reader is set to mix for 10 sec prior to reading. The assay is followed in a fluorescence plate reader—Molecular Devices Spectramax GeminiXS. A 1 hour kinetic run is typical with a reading of the samples being taken every minute. Ex=480 nm (25 nm less than 505 nm, the absorbance maximum for the BODIPY-CE), Em=511 nm (the emission maximum for the BODIPY-CE), Cutoff filter=495 nm. The photomultiplier tube is set at medium. Calibration is set at 6.

Data Evaluation:

Over the course of an hour the assay kinetics appear as a breaking curve. An initial rate is obtained (RFU/sec) for the linear portion of the curve, often 0-500 sec. Rates of samples with inhibitors are compared to an uninhibited DMSO only positive control to determine the apparent percent inhibition (% inhibition apparent). Percent inhibition vs. log of inhibitor concentration is plotted and fit to Sigmoid, 4 parameter equation to calculate $IC_{50}$.

In addition, a test is made on those compounds showing greater than 25% inhibition for their ability to quench a signal independent of ability to inhibit enzyme. This is done with a parallel uninhibited reaction by first measuring the end fluorescence of this uninhibited control (first read). To this well is added a test level of compound and the fluorescence is again read (second read). The percent inhibition due to quench alone is calculated from the formula:

% inhibition due to quench=[(first read−second read)/first read]×100%

True percent inhibition is determined from the formula:

True percent inhibition=[% inhibition apparent−% inhibition due to quench]

Example 2

Assay of CETP in Buffered Plasma

CETP Enzyme

In this example, recombinant human CETP was obtained from CETP-expressing CHO cells rather than being purchased. Final CETP enzyme concentration is approximately 0.8 nM in plasma. Enzyme is stored frozen at −70° C.

Assay Conditions and Protocol

Assay temperature: 25° C.

Final Concentrations in a 150 μl Volume:

54 ng/μl Donor Particles 30.2 ng/μl Acceptor Particles

1×CETP buffer

CETP to 0.8 nM final

2% DMSO (or other solvent)—if compounds are being tested

Protocol:

Use a Dynex Microfluor 2 U-bottom black 96-well plates (Cat# 7205).

Prepare an assay cocktail containing 3 μL of CETP, 50 μL of plasma or serum and 47 μL of 1×buffer, and add 100 μl to plate with multichannel pipettor. In this example, volumes of added buffer are adjusted from prep to prep to keep the concentrations of CETP the same.

Add compounds being tested in DMSO (or DMSO only) in a volume of 3 μl with multichannel pipettor.

Mix plate for 30 sec @ 850 rpm on Eppendorf Thermomixer R plate shaker.

Compounds may be preincubated in solvent (usually DMSO) for up to 15 minutes at 25° C.

Prepare a second assay cocktail containing donor, acceptor, and 1×buffer and add 47 μl to plate with multichannel pipettor to start the assay. Set plate reader to mix for 10 sec prior to reading.

Follow assay in a fluorescence plate reader, a Molecular Devices Spectramax GeminiXS. Set up for a 1-hour kinetic run reading the samples every minute. Ex=480 nm (25 nm less than 505 nm, the absorbance maximum for the Bodipy-CE), Em=511 nm (this is the emission maximum for the Bodipy-CE, Cutoff filter=495. Photomultiplier tube setting of medium, calibration on, 6 reads/well.

Data Evaluation:

As described for example 1.

Example 3

Assay of Native CETP in Buffered Plasma

CETP Enzyme

CETP is present in the plasma or serum fraction. Plasma or sera may be from human, rabbit or transgenic mouse donors. Use of the plasma or serum fraction allows the assay of CETP activity ex vivo in animals treated with a CETP inhibitor. Measurements using CETP in plasma or serum are possible in this assay, whereas the same measurements cannot be made in assays without a quencher because of the high background fluorescence.

Assay Conditions and Protocol:

Assay temperature: 25° C.

Final Concentrations in a 150 µL Volume:

5 ng/µl Donor Particles 17 ng/µl Acceptor Particles

1×CETP buffer

Protocol:

Use a Dynex Microfluor 2 U-bottom black 96-well plates (Cat# 7205).

Prepare an assay cocktail containing only 1×buffer and add 90-95 µl to the plate with a multichannel pipettor.

Add 5-10 µL of each plasma or serum sample to be tested for CETP activity to an assay well. (Rabbits may require 15 µL of plasma or serum). Perform triplicate determinations for each animal sample.

Prepare a second assay cocktail containing donor, acceptor, and 1×buffer, and add 50 µl to the plate with multichannel pipettor to start the assay. Set the plate reader to mix for 10 sec prior to taking a reading.

Follow the assay in a fluorescence plate reader—Molecular Devices Spectramax GeminiXS. Set up for a 1 hour kinetic run reading the samples every minute. Ex=480 nm (25 nm less than 505 nm, the absorbance maximum for the BODIPY-CE), Em=511 nm (the emission maximum for the BODIPY-CE), Cutoff filter=495. Photomultiplier tube setting of medium, calibration on, 6 reads/well.

Data Evaluation:

Same as Example 1.

Results

FIG. 1 shows a plot of multiple assays using the protocol of Example 2. In these assays, serum is present from the CETP. Additional serum from wild type mice (which adds no additional CETP activity) is added to the assay mixture to increase the amount of serum to the amount shown to the right of each plot (5 µL to 50 µL). Donor concentration is initially the amount stated in the protocol. To compensate for the increase in acceptor particles that are present in the serum, the amount of donor is increased 2-fold, 4-fold, 8-fold, and 10-fold, as shown in the plot. This increases the amount of fluorescence from the donor particles. The background fluorescence is still low enough with the added donor particles that accurate measurements can be obtained.

What is claimed is:

1. A method of measuring fluorescence, wherein said fluorescence is used to measure the CETP catalyzed transfer of a non-polar fluorescent ester between lipoprotein particles, comprising the steps of:
   (A) Preparing a suspension comprising:
      (1) A synthetic donor lipoprotein particle which comprises (a) a lipophilic non-polar cholesteryl ester of a fluorescent molecule which comprises the fluorescent heterocyclic BODIPY ring system, (b) an apolipoprotein, (c) a fluorescence quencher, said fluorescence quencher being effective in quenching fluorescence emitted by said lipophilic non-polar fluorescent ester, stable to diffusion, and not diffused by CETP; (d) a triglyceride, and (e) a phospholipid;
      (2) An acceptor lipoprotein particle selected from the group consisting of a native lipoprotein particle and a synthetic high density lipoprotein particle; and
      (3) A buffered solution which comprises CETP;
   (B) Irradiating said suspension with light which stimulates fluorescence from said fluorescent ester; and
   (C) Measuring the fluorescence from said fluorescent ester at one or more times after said suspension is prepared.

2. The method of measuring fluorescence as recited in claim 1, wherein said lipophilic non-polar fluorescent ester is BODIPY-CE.

3. The method of measuring fluorescence as recited in claim 1, wherein said synthetic donor particle is a synthetic HDL particle and said acceptor particle is selected from the group consisting of a native HDL particle, a synthetic HDL particle, a native LDL particle, a native VLDL particle, and a native IDL particle.

4. The method of measuring fluorescence as recited in claim 1, wherein said synthetic donor particle is a synthetic HDL particle and said acceptor particle is a native LDL particle.

5. The method of measuring fluorescence as recited in claim 1, wherein said fluorescence quencher is effective in quenching >85% of the fluorescence emitted by said lipophilic non-polar fluorescent ester, and is stable to diffusion so that >95% of said quencher remains in a donor particle for at least one month after said donor particle is prepared.

6. The method of measuring fluorescence as recited in claim 5, wherein said fluorescence quencher is stable to diffusion so that >98% of said quencher remains in a donor particle for at least one month after said donor particle is prepared.

7. The method of measuring fluorescence as recited in claim 1, wherein said buffered solution comprises native human CETP in plasma or serum.

8. The method of measuring fluorescence as recited in claim 1, wherein said buffered solution comprises recombinant human CETP.

9. The method of measuring fluorescence as recited in claim 1, wherein said donor particle is a synthetic HDL particle which comprises (a) BODIPY-CE, (b) apoHDL, (c) a fluorescence quencher, wherein said fluorescence quencher is effective in quenching >85% of the fluorescence emitted by said lipophilic non-polar fluorescent ester and is stable to diffusion so that >95% of said quencher remains in a donor particle at least one month after said donor particle is synthesized, (d) a triglyceride, and (e) a phospholipid;
   said acceptor particle is a native LDL particle; and said buffered solution comprises recombinant or native human CETP.

10. The method of measuring fluorescence as recited in claim 9, wherein said fluorescence quencher is 4-(4-(dimethylaminophenyl)azo)benzoic acid dicetylamide.

11. A method of measuring the rate of CETP-catalyzed transfer of a lipophilic non-polar fluorescent cholesteryl ester between lipoprotein particles, comprising the steps of:
(A) Preparing a suspension which comprises:
   (1) A synthetic donor lipoprotein particle which comprises (a) a lipophilic non-polar fluorescent cholesteryl ester containing a BODIPY group, (b) an apolipoprotein, (c) a fluorescence quencher, said fluorescence quencher being effective in quenching the fluorescence emitted by said lipophilic non-polar fluorescent ester, stable to diffusion, and not diffused by CETP, (d) a triglyceride, and (e) a phospholipid;
   (2) An acceptor lipoprotein particle selected from a native lipoprotein particle and a synthetic high density lipoprotein particle; and
   (3) A buffered solution which comprises CETP;
(B) Irradiating said suspension with light at a wavelength which stimulates fluorescence from said fluorescent ester;
(C) Measuring the fluorescence from said fluorescent ester at one or more times after said suspension is prepared; and
(D) Computing the rate of transfer of said cholesteryl ester containing a BODIPY group from said donor particle using the fluorescence measurements of step (C).

12. The method of measuring the rate of CETP-catalyzed transfer of a lipophilic non-polar fluorescent cholesteryl ester between lipoprotein particles as recited in claim 11, wherein
said synthetic donor lipoprotein particle is a synthetic HDL particle which comprises apoHDL as the apolipoprotein;
said lipophilic non-polar fluorescent cholesteryl ester is BODIPY-CE; and
said acceptor lipoprotein particle is native LDL.

13. The method of measuring the rate of CETP-catalyzed transfer of a lipophilic non-polar fluorescent cholesteryl ester between lipoprotein particles as recited in claim 12, wherein said fluorescence quencher is 4-(4-(dimethylaminophenyl)azo)benzoic acid dicetylamide.

* * * * *